US006830764B2

(12) United States Patent
Inui et al.

(10) Patent No.: US 6,830,764 B2
(45) Date of Patent: Dec. 14, 2004

(54) METHOD FOR DENATURING ALLERGENS

(75) Inventors: Keiichiro Inui, Matsubara (JP); Mariko Mikame, Tsu (JP)

(73) Assignees: Shinto Fine Co., Ltd., Osaka (JP); Sumitomo Chemical Co., Ltd., Osaka (JP)

(*) Notice: Subject to any disclaimer, the term of this patent is extended or adjusted under 35 U.S.C. 154(b) by 157 days.

(21) Appl. No.: 09/802,941

(22) Filed: Mar. 12, 2001

(65) Prior Publication Data

US 2001/0048097 A1 Dec. 6, 2001

(30) Foreign Application Priority Data

Mar. 14, 2000 (JP) ........................................ 2000-070918

(51) Int. Cl.$^7$ ........................ A01N 59/00; A01N 59/06; A01N 59/08; A01N 59/12; A01N 37/02; A01N 37/04; A01N 37/36; A61K 33/06; A61K 33/14; A61K 31/19

(52) U.S. Cl. ........................ 424/669; 424/600; 424/677; 424/678; 424/682; 424/686; 424/687; 424/689; 424/715; 424/718; 424/722; 424/723; 514/356; 514/547; 514/552; 514/556; 514/557; 514/563; 514/574; 514/826

(58) Field of Search ................................ 424/600, 669, 424/677, 678, 682, 686–689, 715, 718, 722, 723, 602, 675, 693–696; 514/356, 547, 552, 556, 557, 563, 574, 826

(56) References Cited

U.S. PATENT DOCUMENTS

| | | | |
|---|---|---|---|
| 4,350,686 A | * | 9/1982 | Relyveld et al. .............. 424/88 |
| 4,594,239 A | | 6/1986 | Pluim, Jr. |
| 4,997,642 A | | 3/1991 | Curtis et al. |
| 5,094,871 A | | 3/1992 | Heath |
| 5,192,566 A | | 3/1993 | Cox et al. |
| 2002/0150540 A1 | * | 10/2002 | Yoshikawa et al. ........... 424/43 |
| 2003/0203035 A1 | * | 10/2003 | Hasan et al. ................. 424/489 |

FOREIGN PATENT DOCUMENTS

| | | |
|---|---|---|
| CN | 1090466 A | 8/1994 |
| DE | 3525476 A1 | 1/1987 |
| FR | WO8906133 A | 7/1989 |
| FR | 0460332 A1 | 12/1991 |
| GB | 997975 | 7/1965 |
| JP | 1230659 | 9/1989 |
| JP | 2233793 | 9/1990 |
| JP | 5025011 A | 2/1993 |
| JP | 7187902 A | 7/1995 |
| WO | 02/28187 | * 4/2002 |

OTHER PUBLICATIONS

Derwent abstract, accession No. 1987–030107, abstracting DE 3,525,476 (Jan. 1987).*

* cited by examiner

Primary Examiner—John Pak
(74) Attorney, Agent, or Firm—Birch, Stewart, Kolasch & Birch, LLP

(57) ABSTRACT

Application of an alkaline earth metal salt selected from calcium and strontium salts can steadily denature the allergens those exist in the environment without any coloring trouble on the treated material.

7 Claims, No Drawings

METHOD FOR DENATURING ALLERGENS

FIELD OF THE INVENTION

This invention relates to a method for denaturing allergens in the environment.

BACKGROUND ART

A lot of people suffered from allergic diseases like asthma, atopic dermatitis and so on for long years. Mainly house dust mites that live in the house, hair of pets and various kinds of pollens can be the substances that cause these allergic diseases. Recently, treatments those use medicines are applied to allergic patients. On the other hands, removing allergens those cause allergic disease from the environment where allergic patients live is also a useful method that protects from the exposure of allergens. It is reported in Japan, Europe and the United States of America that removing allergens can improve condition of patients.

Cleaning using a vacuum cleaner or an air conditioner and the use of high-density cover on the bedclothes are applied for removing allergens. However, a vacuum cleaner cannot remove all of the allergens that exist in the house, and an air conditioner can remove allergens that exist only in the atmosphere. Further, high-density cover merely protects allergens inside of bedclothes and is not useful for the allergens that come from the environment. Therefore, these methods are not fully satisfied.

Recently the methods for denaturing allergens chemically have been developed. For example, the methods that use tannic acid (JP Hei-02-016731A) and extracts of tea leaf, gallic acid and so on are proposed. However, it is hard to get steady effectiveness for denaturing allergens using these proposed methods. And these methods make the problem that causes coloring on the materials treated with the proposed denaturing agent.

Generally acaricides are used for controlling house dust mites. However, house dust mites, such as *Dermatophagoides farinae, Dermatophagoides pteronyssinus*, and so on can be the source of allergens even after dying and these dead bodies of house dust mites gradually decompose and release fine particles of allergens. As the results, controlling of house dust mites by applying acaricides is not always useful to remove allergens from the environment.

SUMMARY OF THE INVENTION

The present invention was found as the results of earnest efforts to solve these problems, and provides that use of one or more calcium and/or strontium metal salts gives excellent denaturing efficacy on allergens without any coloring trouble on the treated material and that the treatment of the alkaline earth metal salt selected from calcium and strontium salts can steadily denature the allergens those exist in the environment.

DETAILED DESCRIPTION OF THE INVENTION

As the alkaline earth metal salts of the invention, salts of calcium and strontium can be used. These salts can be acetates, propionates, nitrates, chlorides, bromides, iodides, lactates, carbonates, phosphates, citrates, pantothenates, tartrates, succinates, malonates, malates, nicotinates, glycerates, and gluconates, preferably, acetates, propionates and chlorides.

Typical examples of the alkaline earth metal salt include calcium acetate, calcium propionate, calcium nitrate, calcium chloride, calcium bromide, calcium iodide, calcium lactate, calcium carbonate, calcium phosphate, calcium citrate, calcium pyrophosphate, calcium glycerophosphate, calcium stearoyllactate, calcium pantothenate, calcium tartrate, calcium succinate, calcium malonate, calcium malate, calcium nicotinate, calcium glycerate, calcium gluconate, strontium chloride, strontium bromide, strontium acetate, strontium nitrate and strontium carbonate.

These alkaline earth metal salts can be applied as they are. However, they are usually formulated with liquid or solid carrier, and then applied. The content of alkaline earth metal salts in these formulations (allergen denaturing compositions) is usually from 0.01 to 50% by weight, preferably from 0.1 to 10% by weight.

These allergen denaturing compositions can be liquid, powder, paste and so on, and are not restricted if they can denature allergens in the environment. Especially, liquid formulations are effective and easy to handle. One or more kinds of appropriate solvents, which are liquid carriers, can be used for these formulations to dissolve or disperse the alkaline earth metal salts. The solvents are not restricted and for example, hydrophilic solvents such as water, methyl alcohol, ethyl alcohol, isopropyl alcohol, benzyl alcohol, acetic acid, acetone, dimethylformamide, dimethylacetamide, dimethyl sulfoxide, ethylene glycol, propylene glycol, diethylene glycol, triethylene glycol, dipropylene glycol, hexylene glycol, polyethylene glycol, glycerin, ethylene glycol monomethyl ether, ethylene glycol monoethyl ether, ethylene glycol monobutyl ether, ethylene glycol monoethyl ether acetate, gamma-butyrolactone, sulfolane and so on, hydrophobic solvents such as dimethylnaphthalene, dodecylbenzene, liquid paraffin, isophorone, kerosene, dibutyl adipate, diethyl phthalate, diethylene glycol monobutyl ether acetate, propylene carbonate, palm oil, rapeseed oil, cottonseed oil, castor oil, soy bean oil and so on. Usually water, alcohols or their mixture are conveniently used.

The present allergen denaturing composition which is an acidic liquid formulation is more effective and the formulation containing an organic acid or phosphoric acid is useful. Examples of the organic acids include citric acid, lactic acid, malic acid, tartaric acid, malonic acid, succinic acid, ascorbic acid, isoascorbic acid, acetic acid, propionic acid, gluconic acid, maleic acid, fumaric acid and alginic acid. Examples of the phosphoric acid include orthophosphoric acid, metaphosphoric acid, pyrophosphoric acid and polyphosphoric acid. Among them, citric acid, lactic acid, malic acid, tartaric acid, ascorbic acid, isoascorbic acid and phosphoric acid are preferably used. The content of these organic acids is generally from 0.01 to 20% by weight, and preferably from 0.1 to 10% by weight in the formulation.

The present allergen denaturing composition can be any formulation, which is exemplified by aqueous liquid, spray, aerosol, paste and powder. When the present allergen denaturing composition is liquid for spraying, addition of water-soluble polymer compound is effective to prevent scattering of powder after dried. Examples of the water-soluble polymer compound include polyvinyl alcohol, polyacrylic acid, polyacrylic acid salts, polyethylene glycol and polyvinylpyrrolidone. The content of the water-soluble polymer compound is generally from 0.01 to 20% by weight, and preferably from 0.1 to 10% by weight in the formulation.

The present allergen denaturing composition can be applied with the other allergen denaturing agents. And for the purpose of removing house dust mite allergens, it is effective to apply the present allergen denaturing composition with acaricides. These acaricides are not restricted if they have lethal activity and/or repellant activity against house dust mites. Examples of the acaricides include benzyl alcohol, benzyl benzoate, phenyl salicylate, cinnamaldehyde, hyssop oil, carrot seed oil, pyrethroid compounds such as natural pyrethrins, phenothrin and permethrin, organophosphate compounds such as fenitrothion, malathion, fenthion and diazinon, dicofol, chlorobenzilate, hexythiazox, tebufenpyrad and pyridaben. The present allergen denaturing composition can also contain a surfactant, chelating agent, anticorrosive agent, antibacterial agent, binder, thickener, perfume, anti-scale agents, antifoaming agents, antistatic agents, softener and so on. Further, it may also comprise a water-soluble polymer.

The present allergen denaturing composition is applied to an environment, especially indoors. The environment is exemplified by things that contact to persons directly, such as carpets, tatami mats, floors, floor covers, bedclothes like futons, sofas, stuffed animals, clothing, curtains, and living spaces in the house, such as wardrobes and closets that keep those things. Generally it is useful for denaturing allergens that the present allergen denaturing composition is directly sprayed to the carpets, tatami mats, bedclothes, curtains, stuffed animals and so on polluted by allergens. And it is also useful to apply the composition directly to the bedclothes polluted by allergens like starching laundry. Further, it is useful to cover cotton fabrics or nonwoven fabrics applied the compositions on the bedclothes. The application of the present allergen denaturing composition does not cause any coloring troubles. It is desirable to treat acaricides, wash by a washing machine or vacuum out by a vacuum cleaner for highly polluted things by house dust mites.

By the present invention, it is possible to denature most of allergens that is originated from mites, hair or epithelium of pets like dogs and cats, cockroaches, feathers, fungi, plant allergens and so on. The mites of allergen include cheyletid mites, grain mites and so on, especially the house dust mites like *Dermatophagoides farinae* and *Dermatophagoides pteronyssinus* which are important as the cause of dust mite allergy. Not only these mites themselves, but their bodies and feces also cause strong allergens.

Fungi easily grow in humid places, and cause allergens when swallowed into human lungs. Concerning plant allergens, pollens of many kinds of plants, for example, cedar, Japanese cypress, *Zelcova serrata, Amhrosia artemisiifola, Phleum pratense, Artemisia princeps, Anthoxanthum odaratum*, and so on are known. As the results, it is possible to decrease many kinds of allergens practically. Therefore, the invention works effectively on the allergens, particularly on the mite allergens from house dust mites and plant allergens in the environment.

EXAMPLES

The present invention is more precisely described in the following examples and experiments, and is not restricted by these examples and experiments.

Examples 1–17

Each of the components described in Tables 1, 2 and 3 was well mixed to give a homogeneous liquid of the present allergen denaturing composition.

TABLE 1

Composition of examples

| Example Nos. | 1 | 2 | 3 | 4 | 5 | 6 |
|---|---|---|---|---|---|---|
| Calcium chloride dihydrate | 2 | 2 | 2 | — | 2 | 2 |
| Strontium chloride hexahydrate | — | — | — | 2 | — | — |
| Lactic acid | — | 2 | 2 | 2 | 2 | 2 |
| Polyacrylic acid | — | — | — | — | 1 | — |
| Polyethylene glycol 20000 | — | — | — | — | — | 1 |
| Ethanol | 15 | 15 | 15 | 15 | 15 | 15 |
| Benzyl alcohol | — | — | 5 | 5 | 5 | 5 |
| Water | 83 | 81 | 76 | 76 | 75 | 75 |

The numbers are % by weight.

TABLE 2

Composition of examples

| Example Nos. | 7 | 8 | 9 | 10 | 11 | 12 |
|---|---|---|---|---|---|---|
| Calcium chloride dihydrate | 2 | 2 | 2 | 2 | — | — |
| Calcium lactate pentahydrate | — | — | — | — | 2 | 2 |
| Citric acid | 2 | — | — | — | — | — |
| Malic acid | — | 2 | — | — | — | — |
| Tartaric acid | — | — | 2 | — | — | — |
| Phosphoric acid | — | — | — | 1 | 2 | — |
| Lactic acid | — | — | — | — | — | 6 |
| Polyvinylpyrrolidone | 1 | 1 | 1 | 1 | 1 | 1 |
| Ethanol | 15 | 15 | 15 | 15 | 15 | 15 |
| Benzyl alcohol | 5 | 5 | 5 | 5 | 2 | 2 |
| Water | 75 | 75 | 75 | 76 | 78 | 74 |

The numbers are % by weight.

TABLE 3

Composition of examples

| Example Nos. | 13 | 14 | 15 | 16 | 17 |
|---|---|---|---|---|---|
| Strontium chloride | 2 | — | — | — | — |
| Calcium acetate monohydrate | — | 2 | — | — | — |
| Calcium propionate | — | — | 2 | — | — |
| Calcium glycerophosphate | — | — | — | 2 | — |
| Calcium phosphate hexahydrate | — | — | — | — | 2 |
| Lactic acid | — | — | — | 2 | 2 |
| Polyethylene glycol 20000 | 0.5 | 0.5 | 0.5 | 0.5 | 0.5 |
| Ethanol | 15 | 15 | 15 | 15 | 15 |
| Water | 82.5 | 82.5 | 82.5 | 80.5 | 80.5 |

The numbers are % by weight.

To provide for the Experiments below, the reference compositions were prepared by mixing the components described in Table 4. These reference compositions contain salts except calcium salts and strontium salts.

Reference Compositions 1–6

TABLE 4

Composition of references

| Reference Example Nos. | 1 | 2 | 3 | 4 | 5 | 6 |
|---|---|---|---|---|---|---|
| Zinc chloride | 2 | — | — | — | — | — |
| Bismuth chloride | — | 2 | — | — | — | — |
| Lithium chloride | — | — | 2 | — | — | — |
| Indium chloride tetrahydrate | — | — | — | 2 | — | — |
| Magnesium chloride hexahydrate | — | — | — | — | 2 | — |
| Gallic acid | — | — | — | — | — | 3 |
| Lactic acid | 2 | 2 | 2 | 2 | 2 | — |
| Ethanol | 15 | 15 | 15 | 15 | 15 | 15 |

TABLE 4-continued

Composition of references

| Reference Example Nos. | 1 | 2 | 3 | 4 | 5 | 6 |
|---|---|---|---|---|---|---|
| Benzyl alcohol | 5 | 5 | 5 | 5 | 5 | — |
| Water | 76 | 76 | 76 | 76 | 76 | 82 |

The numbers are % by weight.

Experiment 1

Measurement of Denaturing Efficacy for Dust Mite Allergen Der 2

Approximately 0.03 gram of standard house dust (contains approximately 1000 micrograms/gram of mite Der 2 allergen) was rubbed over the felt (6.6 cm in diameter), and the compositions 1 to 17 and reference compositions 1 to 6 were sprayed on the house dust using trigger type spray. After dried in room temperature for 5 hours, the felt was put into a polyethylene bag and the mite allergen of the felt was extracted with 10 ml phosphate buffered saline (pH 7.0, containing 15% by weight of Bovine Serum Albumin) by crumpling for one minute. The extracted solution was centrifuged for 60 minutes with 12,000 rpm, and the amount of the mite allergen of the supernatant was estimated by the simple detecting kit for the house mite allergen, MITEY CHECKER (product of SHINTO FINE Co., Ltd.). The standard for intensity of the color change for detecting the mite allergen was listed in Table 5. Further, the amount of mite allergen was measured by sandwich method of Enzyme Linked Immunosorbent Assay (ELISA). First, 1000 ng/microliter solution of Derf 2 monoclonal antibody (13A4) was diluted into 500 times, and 100 microliters of the diluted solution was put into F16 MAXISORP NUNC-IMMUNO MODULE plate (product of NUNC company) in each well. Then the plate was coated at 4° C. for more than one day. After coating, the solution was removed, and blocking reagent {one percent by weight of Bovine Serum Albumin fraction five (NACALAI TESQUE INC.) with phosphate buffered saline (ph7.2, containing 0.1% by weight of sodium azide)} was added with 100 microliters per well, and reacted at 37° C. for 60 minutes. After the reaction, the plate was rinsed with phosphate buffered saline (pH7.2, containing 0.1% by weight of Tween 20 (commercial name) that is a surfactant mainly consisting of polyoxyethylene-sorbitan monolaurate produced by Atlas Chemical). Ninety microliters of the supernatant sample and 10 microliters of phosphate buffered saline were added per well, and reacted at 37° C. for 60 minutes. Then, Derf 2 monoclonal antibody labeled by peroxidase was diluted into 10 times and 100 microliters per well were added, and the solution was reacted at 37° C. for 60 minutes. o-Phenylenediamine (30 mg tablet, product of SIGMA CHEMICAL Company) and 15 microliters of 30% hydrogen peroxide were added in 15 ml phosphate buffered saline (pH6.2), and 100 microliters of this solution was added into each well of the plate, and reacted at 37° C. for 5 minutes. Then, 50 microliters of 2 mol/L sulfuric acid was added immediately into each well, and the absorbance was measured using a spectrophotometer for micro-plate (product of Bio-Rad Laboratories Inc.). Blank sample was conducted in the same way except for examples or referenced samples. The results were shown in Table 6.

TABLE 5

The standard for intensity of the color change for detecting the mite allergen

| Score | Intensity of the color change | Amount of mite allergen |
|---|---|---|
| ++ | Thick, apparent line | >35 micro grams (>350 mites) |
| + | Apparent line | 10 micro grams (100 mites) |
| ± | Slight color change | 5 micro grams (50 mites) |
| − | No color change | <1 micro gram (<10 mites) |

TABLE 6

Results of denaturing efficacy of the examples for mite allergen

| | Score of Mitey Checker | ELISA (microgram) | Denaturing ratio (%) |
|---|---|---|---|
| Blank | ++ | 27 | — |
| Example 1 | ± | 7 | 74 |
| Example 2 | − | 4 | 85 |
| Example 3 | − | 3 | 89 |
| Example 4 | − | 1 | 96 |
| Example 5 | − | 1 | 96 |
| Example 6 | − | 1 | 96 |
| Example 7 | − | 2 | 93 |
| Example 8 | − | 2 | 93 |
| Example 9 | − | 2 | 93 |
| Example 10 | − | 1 | 96 |
| Example 11 | − | 1 | 96 |
| Example 12 | − | 1 | 96 |
| Example 13 | − | 1 | 96 |
| Example 14 | − | 2 | 93 |
| Example 15 | − | 2 | 93 |
| Example 16 | − | 4 | 85 |
| Example 17 | − | 3 | 89 |
| Reference 1 | ++ | 20 | 26 |
| Reference 2 | ++ | 24 | 11 |
| Reference 3 | ++ | 25 | 7 |
| Reference 4 | ++ | 23 | 15 |
| Reference 5 | ++ | 26 | 4 |
| Reference 6 | ++ | 22 | 19 |

Experiment 2

Measurement of Denaturing Efficacy of the Example 6 for Cedar Pollen Allergen Cry j 2

Zero, 16, 20 and 24 microliters of the composition obtained in example 4 were reacted with the extract of cedar pollen {5 micrograms per microliter of carbonate-bicarbonate buffered solution (pH9.5)}, and coated to Linbro/Titertek E.I.A. Microtitration plate (product of ICN BIOCHEMICAL INC.) at 4° C. overnight. After coating, the plate was rinsed with phosphate buffered saline (pH7.2, containing 0.1% by weight of Tween 20). Then, cedar pollen antibody Anti-Cry j-2 (Lot.747032) was diluted into 200 times with phosphate buffered saline (pH7.2, containing one percent by weight of Bovine Serum Albumin and 0.1% by weight of Tween 20), and added with 50 microliters per well, and the solution was reacted at 37° C. for 60 minutes. After reacting, the plate was rinsed with phosphate buffered saline (pH7.2, containing 0.1% by weight of Tween 20). HRP-Anti-Rabbit IgG(gamma chain) mouse monoclonal antibody (SIGMA CHEMICAL Company, Lot. 097H4852) was diluted into 5000 times with phosphate buffered saline (pH7.2, containing 0.1% by weight of Tween 20), and added with 50 microliters per well, and of the solution was reacted at 37° C. for 60 minutes. After reaction, the plate was rinsed with phosphate buffered saline (pH7.2, containing 0.1% by weight of Tween 20, and then with distilled water. o-Phenylenediamine (30 mg tablet, product of SIGMA CHEMICAL Company) and 15 microliters of 30% hydrogen peroxide were added in 15 ml phosphate buffered saline (pH6.2), and 100 microliters of this solution was added into each well of the plate, and reacted at 37° C. for 15 minutes. Then, 50 microliters of 2 mol/L sulfuric acid was added immediately into each well, and the absorbance was measured using a spectrophotometer for micro-plate (product of Bio-Rad Laboratories Inc.). The results were shown in Table 7.

TABLE 7

Results of denaturing efficacy of example 6 for cedar pollen allergen Cry j2

| Added example 6 (micro liter/well) | The amount of cedar pollen allergen (absorbance OD490 nm) | Denaturing ratio (%) |
|---|---|---|
| 0 | 0.795 | 0 |
| 16 | 0.198 | 75.1 |
| 20 | 0.122 | 84.7 |
| 24 | 0.076 | 90.4 |

Experiment 3
Measurement of Denaturing Efficacy for Dust Mite Allergen Der 2 by Treating on Carpet Virgin carpets (50 cm×50 cm) were prepared and vacuumed by an electric vacuum cleaner for more than 1 minute. Approximately 50 mg of pooled house dust (contains approximately 1 mg/g of mite allergen Der 2) were rubbed over each carpet, and the composition obtained in example 4 and 13, reference 5 and 6 were sprayed on the carpet. The sprayed amount was approximately 40 g per 1 carpet of each sample, respectively. After being dried at room temperature for 5 hours, house dust on the surface of each carpet was collected using a vacuum cleaner with DUST SAMPLER (product of SHINTO FINE Co., Ltd.) and MITEY-FELT (product of SHINTO FINE Co.,Ltd.) for one minute. Each MITEY-FELT was put into a polyethylene bag and mite allergen of the felt was extracted in the 10 ml phosphate buffered saline (pH7.2, containing 10% by weight of Skim milk and 15% by weight of Bovine Serum Albumin) by crumpling for one minute. The extracted solution was centrifuged for 60 minutes with 12,000 rpm, and the amount of mite allergen of the supernatant was measured by MITEY CHECKER and the ELISA method. Blank sample was conducted in the same way except for spraying of the examples and/or references. The results were shown in Table 8.

TABLE 8

Results of denaturing efficacy of the examples for mite allergen Der 2

| | Score of MITEY CHECKER | ELISA (micro gram) | Denaturing ratio (%) |
|---|---|---|---|
| Blank | ++ | 47 | — |
| Example 6 | − | Less than 1 | More than 98 |
| Example 12 | − | 1 | 98 |
| Reference 5 | ++ | 44 | 6 |
| Reference 6 | ++ | 39 | 17 |

Experiment 4
Coloring Test for Cotton Fabrics

The composition obtained in Example 6 and 3% aqueous solution of tannic acid were treated on the surface of three pieces of cotton fabrics (20 cm×20 cm), respectively. The treated amount was approximately 4 g per 1 fabric. One of three cotton fabrics was washed using a commercial detergent (ATTACK, product of KAO Corporation), and the other one was exposed to sunshine for 5 hours. Chroma of these fabrics was measured using chroma meter (CT-210, product of MINOLTA Company). The value L* means whiteness and is whitish as near as 100. The value b* means tints and is yellowish as larger than 0 and bluish as less then 0. Results were shown in Table 9.

TABLE 9

Results of coloring test

| | Blank | Example 6 | Tannic acid soln. |
|---|---|---|---|
| L* (initial) | 91.6 | 91.4 | 91.0 |
| L* (washed) | 91.3 | 91.4 | 87.3 |
| L* (exposed) | 91.3 | 91.3 | 89.8 |
| b* (initial) | 0.5 | 0.3 | 2.6 |
| b* (washed) | −0.1 | −0.1 | 5.8 |
| b* (exposed) | 0.4 | 0.3 | 3.2 |

What is claimed is:

1. A method for denaturing allergens originated from mites, hair or epithelium of pets, cockroaches, feathers, fungi and pollens of plants which comprises applying an effective amount of a calcium or strontium salt selected from the group consisting of acetate, propionate, nitrate, chloride, bromide, iodide, lactate, carbonate, citrate, pantothenate, tartrate, succinate, malonate, malate, nicotinate, glycerate, stearoyllactate and gluconate to a place where allergens exist or will exist.

2. A method for denaturing allergens according to claim 1, wherein the salt is a salt of calcium.

3. A method for denaturing allergens originated from mites, hair or epithelium of pets, cockroaches, feathers, fungi and pollens of plants which comprises applying an effective amount of a calcium salt selected from the group consisting of calcium acetate, calcium propionate, calcium nitrate, calcium chloride, calcium bromide, calcium iodide, calcium lactate, calcium carbonate, calcium citrate, calcium pyrophosphate, calcium glycerophosphate, calcium stearoyllactate, calcium pantothenate, calcium tartrate, calcium succinate, calcium malonate, calcium malate, calcium nicotinate, calcium glycerate and calcium gluconate.

4. A method for denaturing allergens according to claim 1, wherein the salt is a salt of strontium.

5. A method for denaturing allergens according to claim 4, wherein the salt is a strontium chloride.

6. The method for denaturing allergens according to claim 1, wherein the allergens are originated from mites.

7. The method for denaturing allergens according to claim 1, wherein the salt is acetate, propinate or chloride.

* * * * *